(12) United States Patent
Fallet et al.

(10) Patent No.: US 8,796,641 B2
(45) Date of Patent: Aug. 5, 2014

(54) INSTALLATION FOR TREATING ARTICLES BY ELECTRON BOMBARDMENT

(71) Applicant: Serac group, La Ferte Bernard (FR)

(72) Inventors: Remy Fallet, Souvigne sur Meme (FR); Delphine Gueguen, Cherreau (FR)

(73) Assignee: Serac Group, La Ferte Bernard (FR)

( * ) Notice: Subject to any disclaimer, the term of this patent is extended or adjusted under 35 U.S.C. 154(b) by 0 days.

(21) Appl. No.: 13/673,667

(22) Filed: Nov. 9, 2012

(65) Prior Publication Data

US 2013/0140470 A1    Jun. 6, 2013

(30) Foreign Application Priority Data

Nov. 10, 2011    (FR) ...................... 11 60242

(51) Int. Cl.
*A61L 2/08* (2006.01)
*A61L 2/02* (2006.01)
*G21K 5/08* (2006.01)

(52) U.S. Cl.
CPC .............. *G21K 5/08* (2013.01); *A61L 2202/23* (2013.01); *A61L 2/087* (2013.01); *A61L 2202/121* (2013.01)
USPC ............ 250/455.11; 250/453.11; 250/454.11; 250/492.1; 250/492.3; 422/22; 422/23

(58) Field of Classification Search
USPC .................... 422/22, 23; 250/453.11, 454.11, 250/455.11, 492.1, 492.3
See application file for complete search history.

(56) References Cited

U.S. PATENT DOCUMENTS

2011/0012030 A1* 1/2011 Bufano et al. ............. 250/492.3

FOREIGN PATENT DOCUMENTS

| EP | 2052744 | 4/2009 |
|---|---|---|
| EP | 2138298 | 12/2009 |
| EP | 2371397 | 10/2011 |
| WO | WO2009095182 | 8/2009 |

* cited by examiner

*Primary Examiner* — Nicole Ippolito
(74) *Attorney, Agent, or Firm* — Muncy, Geissler, Olds & Lowe, P.C.

(57) ABSTRACT

An installation for treating articles with radiation, the installation comprising a structure having pivotally mounted thereon an inlet starwheel and an outlet starwheel respectively arranged facing an inlet and an outlet of a shielded enclosure in which there are mounted at least one pivotal treatment starwheel and at least one electron emitter in the vicinity of the treatment starwheel. The installation comprises a linear inlet conveyor and a linear outlet conveyor extending inside the shielded enclosure respectively facing the inlet and the outlet, the linear conveyors each comprising a respective transporter surrounding a shielded wall forming a baffle.

4 Claims, 1 Drawing Sheet

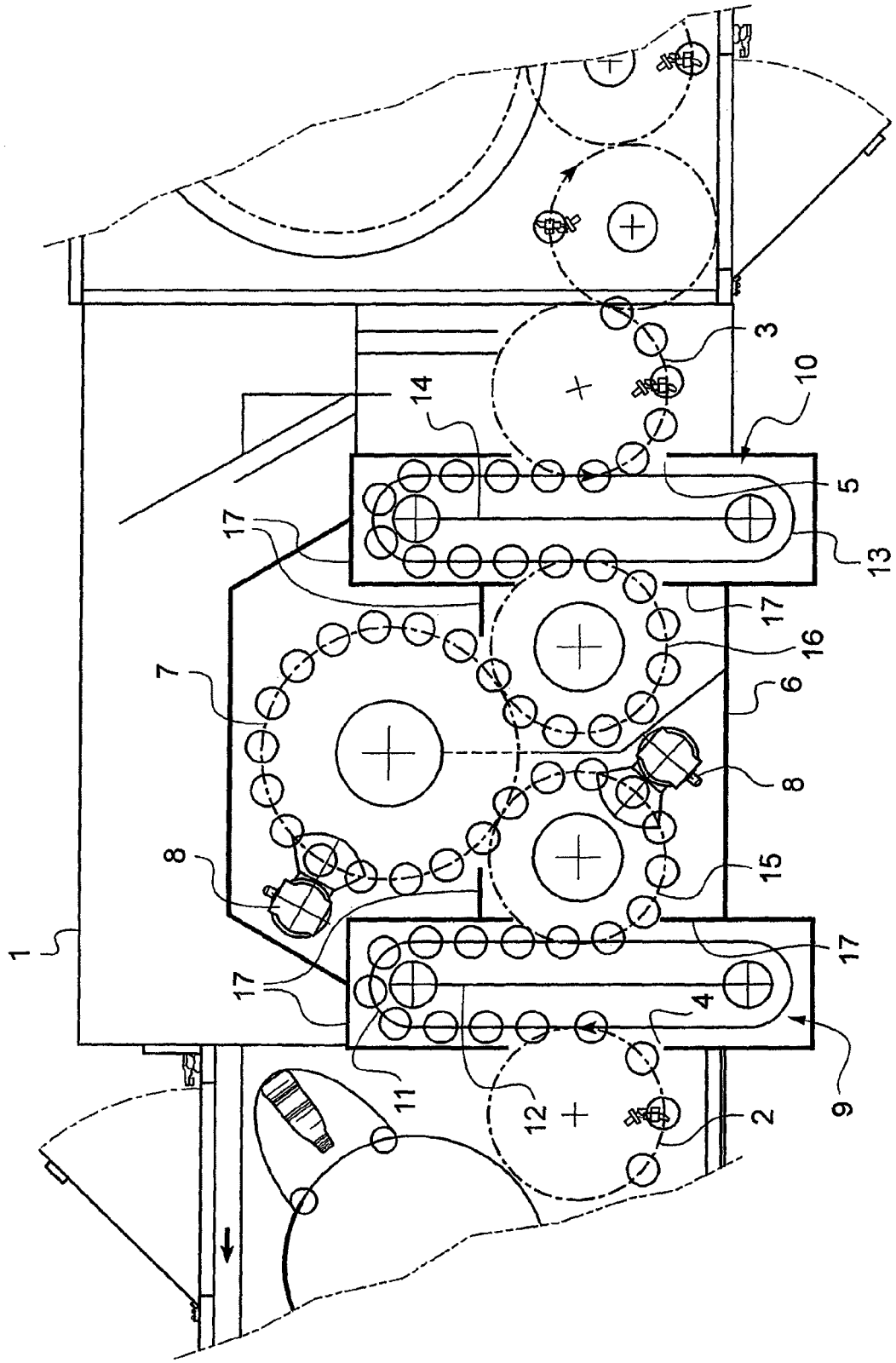

INSTALLATION FOR TREATING ARTICLES BY ELECTRON BOMBARDMENT

FIELD OF THE INVENTION

The present invention relates to an installation for treating articles by radiation, and more particularly by electron bombardment.

It is known to sterilize containers by subjecting them to electron bombardment.

Electron bombardment is performed in a shielded enclosure seeking to confine X-rays in a zone from which operators are excluded.

BACKGROUND OF THE INVENTION

To this end, an installation for treating containers by electron bombardment comprises a structure having pivotally mounted thereon an inlet starwheel and an outlet starwheel that are arranged respectively facing an inlet and an outlet of a shielded enclosure in which there are mounted a pivoting treatment starwheel and one or more electron emitters in the vicinity of the treatment starwheel. The starwheels are provided with gripper means for holding the containers so that the containers pass from one starwheel to another from the inlet towards the outlet.

In order to attenuate the energy of the X-rays emitted by the emitter and in order to prevent them from leaving the shielded enclosure, it is known to place shielded internal partitions inside the enclosure, which partitions are arranged as baffles towards the inlet and the outlet of the shielded enclosure. A "baffle" arrangement means an arrangement in which the internal partitions are arranged so as to prevent any direct path for X-rays from the emitter to the inlet or to the outlet. Thus, X-rays emitted by the emitter towards the containers are reflected against the walls of the shielded enclosure and the shielded internal partitions a sufficiently large number of times to ensure that they have lost most of their energy before reaching the inlet or the outlet of the shielded enclosure.

Installing internal partitions makes it necessary for the treatment starwheel to be remote from the inlet starwheel and the outlet starwheel, thereby making it necessary to provide two internal starwheels that are mounted inside the shielded enclosure so as to be tangential firstly to the treatment starwheel and secondly to the inlet or outlet starwheel respectively through the inlet or the outlet.

Although operator protection is provided very safely in such installations, they present the drawback of being very bulky because of the presence of intermediate starwheels of dimensions that have a direct influence on the length of the path to be traveled by the X-rays in order to escape from the enclosure, and thus on the ability of the enclosure to prevent radiation from escaping.

OBJECT AND SUMMARY OF THE INVENTION

An object of the invention is to provide means for protecting operators acting in the vicinity of an installation for treating articles with radiation while limiting the size of the installation.

To this end, the invention provides an installation for treating articles by electron bombardment radiation, comprising a structure having pivotally mounted thereon an inlet starwheel and an outlet starwheel respectively arranged facing an inlet and an outlet of a shielded enclosure in which there are mounted at least one pivotal treatment starwheel and at least one electron emitter in the vicinity of the treatment starwheel, the starwheels being provided with article-gripper means, the shielded enclosure having internal shielded partitions arranged as baffles. The installation comprises at least one linear conveyor extending inside the shielded enclosure respectively facing the inlet or the outlet, the linear conveyor having a transporter extending as an elongate ring around a shielded wall extending in a longitudinal direction of the transporter in order to form a baffle.

Thus, the shielded wall of the linear conveyor forms a barrage against radiation without increasing the longitudinal size of the installation. In order to reinforce the barrage against radiation, it suffices to lengthen the shielded wall, which can be done without increasing the distance between the inlet and the outlet of the installation. The use of linear conveyors also provides greater flexibility in the arrangement of the installation, thereby making it easier to incorporate in a production line.

Preferably, the installation comprises a linear inlet conveyor and a linear outlet conveyor extending inside the shielded enclosure respectively facing the inlet and the outlet, the linear conveyors each comprising a transporter surrounding a shielded wall extending in a longitudinal direction of the transporter in order to form a baffle at the inlet and a baffle at the outlet, respectively.

BRIEF DESCRIPTION OF THE DRAWINGS

Other characteristics and advantages of the invention appear on reading the following description of particular, non-limiting embodiments of the invention.

Reference is made to the sole accompanying FIGURE that is a diagram of an installation in accordance with the invention.

MORE DETAILED DESCRIPTION

With reference to the FIGURE, the treatment installation in accordance with the invention in this example is arranged for sterilizing containers by subjecting them to electron bombardment.

The installation of the invention is designed to be incorporated in a production line, e.g. downstream from a station for blowing containers and upstream from a station for filling said containers.

The installation comprises a structure 1 having pivotally mounted thereon an inlet starwheel 2 and an outlet starwheel 3, each provided with container-gripper means such as clamps for grasping containers by the neck. Such starwheels are themselves known and are therefore not described in greater detail herein.

The inlet and outlet starwheels 2 and 3 are arranged respectively facing an inlet 4 and an outlet 5 of a shielded enclosure 6 in which a treatment starwheel or platform 7 is pivotally mounted. The treatment starwheel 7 is provided with container-gripper means, such as clamps for holding the containers by the neck, and with emitters mounted facing the clamps. The clamps and the emitters are mounted on the starwheel so as to move relative to one another in a vertical direction in order to insert each emitter into the container supported by the facing clamp. Such a treatment starwheel 7 is itself known and is therefore not described in greater detail herein. A stationary emitter 8 is also mounted in the shielded enclosure 6 in the vicinity of the periphery of the treatment starwheel 7 in order to emit a beam of electrons towards the containers that move past the stationary emitter 8 while the treatment starwheel 7 is rotating.

A linear inlet conveyor 9 and a linear outlet conveyor 10 extend inside the shielded enclosure 6 respectively facing the inlet 4 and the outlet 5 so as to be tangential respectively to the inlet starwheel 2 and the outlet starwheel 3.

The linear inlet conveyor 9 has a transporter 11 extending as an elongate ring around a shielded wall 12 substantially facing the inlet 4.

The linear outlet conveyor 10 has a transporter 13 extending as an elongate ring around a shielded wall 14 substantially facing the outlet 5.

The transporters 11 and 13 are provided with container support means that are themselves known and that serve to transfer the containers from the inlet starwheel 2 to the linear inlet conveyor 9 and from the linear outlet conveyor 10 to the outlet starwheel 3.

The shielded walls 12 and 14 are of length (measured parallel to the long dimension of the corresponding linear conveyor) that is greater than the width (measured parallel to the long dimension of the corresponding linear conveyor) of the inlet 4 and of the outlet 5, respectively. The shielded walls 12, 14 thus form respective baffles at the inlet 4 and at the outlet 5 of the shielded enclosure 6.

Intermediate starwheels 15 and 16 are pivotally mounted inside the shielded enclosure 6. The intermediate starwheel 15 is mounted between the treatment starwheel 7 and the linear inlet conveyor 9 so as to be tangential to both of them. The intermediate starwheels 15 and 16 are themselves known and are provided with container gripper means such as clamps for holding the containers by the neck. A stationary emitter 8 is also mounted in the vicinity of the periphery of the intermediate starwheel 15.

The tangency points where each of the linear conveyors 9, 10 is tangential with a starwheel adjacent thereto are located on the long sides of the transporters 11 and 13 in such a manner that the lengths of the transporter extending on either side of the tangency points are identical to each other. In a variant, these lengths could be different.

The shielded enclosure 6 has shielded internal partitions 17 arranged as baffles. The internal partitions 17 extend from the walls of the shielded enclosure 6 in such a manner that the starwheels and the linear conveyors are separated from one another by internal partitions 17 except in the tangency zones where the internal partitions leave openings of dimensions that are just sufficient to pass containers from the linear inlet conveyor 9 to the intermediate starwheel 15, from the intermediate starwheel 15 to the treatment starwheel 7, from the treatment starwheel 7 to the intermediate starwheel 16, and from the intermediate starwheel 16 to the linear outlet conveyor 10.

The term "shielded" is used to mean that the wall or partition is proof against electrons and X-rays. The wall of the shielded partition thus comprises a layer of lead covered by a sheet of stainless steel.

Naturally, the invention is not limited to the embodiment described, but covers any variant coming within the ambit of the invention as defined by the claims.

In particular, the installation need not have any intermediate starwheels, with the linear conveyors extending tangentially to the treatment starwheel.

The installation may have some other number of intermediate starwheels or of treatment starwheels.

The installation may have emitters on board the treatment starwheel and a plurality of stationary emitters, only one or a plurality of stationary emitters, or only emitters on board the treatment starwheel.

The starwheels may be of a structure other than that described, in particular concerning the way containers are gripped.

The invention may be applied to articles other than containers and/or to other types of radiation.

What is claimed is:

1. An installation for treating articles with radiation, the installation comprising a structure having pivotally mounted thereon an inlet starwheel and an outlet starwheel respectively arranged facing an inlet and an outlet of a shielded enclosure in which there are mounted at least one pivotal treatment starwheel and at least one electron emitter in the vicinity of the treatment starwheel, the starwheels being provided with article-gripper means, the shielded enclosure having internal shielded partitions arranged as baffles, wherein the installation includes at least one linear conveyor extending inside the shielded enclosure facing the inlet or the outlet, the linear conveyor having a transporter extending as an elongate ring around a straight shielded wall extending in a longitudinal direction of a straight portion of the transporter in order to form a baffle, the straight shielded wall facing said inlet or outlet and having a length greater than a width of said inlet or outlet.

2. An installation according to claim 1, including a linear inlet conveyor and a linear outlet conveyor extending inside the shielded enclosure respectively facing the inlet and the outlet, the linear conveyors each comprising a transporter surrounding a shielded wall extending in a longitudinal direction of the transporter in order to form a baffle at the inlet and a baffle at the outlet, respectively.

3. An installation according to claim 1, wherein at least one intermediate starwheel is mounted inside the shielded enclosure between the treatment starwheel and the linear conveyor.

4. An installation according to claim 1, wherein the shielded internal partitions separate the treatment starwheel from the linear conveyor while leaving an opening for passing the articles.

* * * * *